United States Patent [19]

Stähle et al.

[11] 4,271,175

[45] Jun. 2, 1981

[54] METHOD OF USING 2-[N-(2,6-DICHLORO-PHENYL)-N-ALLYL-AMINO]-2-IMIDAZOLINE AND SALTS THEREOF AS BRADYCARDIACS

[75] Inventors: Helmut Stähle; Herbert Köppe; Werner Kummer, all of Ingelheim am Rhein; Dietrich Arndts, Appenheim, all of Fed. Rep. of Germany; Walter Kobinger, Vienna, Austria; Christian Lillie, Vienna, Austria; Ludwig Pichler, Vienna, Austria

[73] Assignee: Boehringer Ingelheim GmbH, Ingelheim am Rhein, Fed. Rep. of Germany

[21] Appl. No.: 55,966

[22] Filed: Jul. 9, 1979

[30] Foreign Application Priority Data

Jul. 15, 1979 [DE] Fed. Rep. of Germany ....... 2831190

[51] Int. Cl.$^3$ .......................................... A61K 31/415
[52] U.S. Cl. ................................................ 424/273 R
[58] Field of Search .................................... 424/273 R

[56] References Cited

U.S. PATENT DOCUMENTS

| | | | |
|---|---|---|---|
| 3,708,485 | 1/1973 | Stahle et al. | 424/273 |
| 3,850,926 | 11/1974 | Stahle et al. | 424/273 |
| 3,969,525 | 7/1976 | Wolf | 424/273 |

*Primary Examiner*—Frederick E. Waddell
*Attorney, Agent, or Firm*—Hammond & Littell, Weissenberger & Muserlian

[57] ABSTRACT

The method of using 2-[N-2,6-Dichloro-phenyl)-N-allyl-amino]-2-imidazoline or a non-toxic acid addition salt thereof as bradycardiacs.

2 Claims, No Drawings

METHOD OF USING 2-[N-(2,6-DICHLORO-PHENYL)-N-ALLYL-AMINO]-2-IMIDAZOLINE AND SALTS THEREOF AS BRADYCARDIACS

This invention relates to the novel method of using 2-[N-(2,6-dichloro-phenyl)-N-allyl-amino]-2-imidazoline or a non-toxic acid addition salt thereof as bradycardiacs.

More particularly, the present invention relates to the method using the above-mentioned imidazoline derivative or a non-toxic, pharmacologically acceptable acid addition salt thereof for prophylaxis and therapy of ischemic cardiac disorders and sinus tachycardias of various origins.

THE PRIOR ART

2-[N-(2,6-Dichloro-phenyl)-N-allyl-amino]-2-imadazoline and its non-toxic acid addition salts are known to have useful pharmacodynamic properties other than bradycardiac activity. The compound and its salts, their preparation, and pharmaceutical compositions containing them as active ingredients are disclosed in Belgian Pat. No. 759,125.

DESCRIPTION OF THE INVENTION

We have made the unobvious and unexpected discovery that 2-[N-(2,6-dichloro-phenyl)-N-allyl-amino]-2-imidazoline and its non-toxic, pharmacologically acceptable acid addition salts slow the heart rate. This discovery was confirmed by pharmacological as well as clinical studies.

The heart rate was reduced after intravenous administration to anesthetized animals; Rat beginning at 0.5 mgm/kg, cat beginning at 0.3 mgm/kg, dog 2.5 mgm/kg. The compound has reduced the heart rate also in the awake animal: in the dog the action of the substance (2.5 mgm/kg intravenously) depends upon the starting rate; weak effect of substance in vagotonic, normal animals, stronger effects after artificial increase of the heart rate by pretreatment with atropine and hydralazine. In the awake rat a decrease in the heart rate has been observed beginning at 5 mgm/kg p.o.

Most of the other cardiovascular parameters were only moderately changed in relation to the bradycardiac effect. After exclusion of the CNS, the substance unfolded its full bradycardiac effect. In the spinal rat, 2.5 mgm/kg i.v. produce a reduction of the heart rate by 150 beats/minute; this indicates a direct action at a cardiac site, which has been confirmed by the decrease of frequency in the isolated spontaneously beating auricle of the guinea pig ($EC_{30}=2.9$ μg/ml). In the electrically stimulated auricle preparation a negative inotropic ($EC_{30}=155$ μg/ml) and antiarrhythmic action (frequency test, $EC_{50}=100$ μg/ml) occurred only in a 53-fold or 34-fold concentration, respectively. The increase in blood pressure in the spinal rat may be considered as indication of a weak α-adreno-ceptor-stimulating effect. The bradycardiac action of 2-[N-(2,6-dichloro-phenyl)-N-allyl-amino]-2-imidazoline is not due to stimulation of cholinergic receptors (no reduction of the effect of the substance by atropine in the auricle of the guinea pig). The substance does not exhibit any β-adreno-receptor blocking effect.

In the anesthetized cat the triple product of systolic blood-pressure x heart beat frequency x left ventricular ejection time was decreased clearly and long-lastingly.

In the myocardischemia test (anesthetized cat, ECG-alterations at short-time coronary occlusion) the signs of ischemia (elevation of $\overline{ST}$ and T) were decreased by 2.5 and 5 mgm/kg i.v. of the substance clearly and long-lastingly (>1 hour). Both findings are indications of a decrease in the myocardial consumption of oxygen due to the substance.

Observations made in the awake dog did not show any central side-effects at 5 mgm/kg i.v.

The above results distinguish the compound clearly from other bradycardiac active substances and groups of substances such as clonidine, antiarrhythmics, calcium antagonists of the verapamil type, cholinergic substances and β-adreno-receptor blockers. Due to its specific decrease of frequency (relief of the heart load) and the experimental findings, indicating a decrease in the myocardial oxygen consumption (triple product, myocard-ischemia test), it is recommended to use the compound for chronic coronary insufficiency.

In a clinical test, one athletically trained and five untrained, healthy male volunteers participated.

The effects of the compounds were determined by means of the following test scheme:

Before administration of 40 mgm of 2-[N-(2,6-dichlorophenyl)-N-allyl-amino]-imidazoline-(2) and 2 hours afterwards in form of gelatine capsules each containing 20 mgm of active ingredient, a stress test was made with the test subjects in fasted condition. The ECG was recorded at rest, and the blood pressure was measured. Then the ECG was registered under stress with the aid of a bicycle ergometer and the blood pressure was measured, where the stress began at 50 watts and was increased by 25 watts each after 3 minutes up to a final wattage of 150. Three minutes after the stress, the ECG was again taken at rest, and the blood pressure was measured. The heart rate was determined by evaluating the ECG. For the ECG at rest, the chest-wall extremity leads were registered; under stress only the chest-wall lead was recorded.

In the five untrained test subjects at rest, the heart rate decreased after administration of the active substance by an average of 12.6 beats/minute, under stress of 50 to 150 watt by an average of 15.0 to 18.2 beats per minute, and after 3 minutes of recovery by an average of 14.4 beat per minute compared to the control value. The maximum single decrease amounted to 28 beats per minute. In one of the five test subjects no decrease was registered at rest. In the athletic test subject no clear decreases of the heart rate showed after medication, compared to the control value. There was only found a maximum decrease of the heart rate by five beats per minute at a wattge of 100.

In two of the untrained test subjects, there occurred under effect of the test compound the following changes in the course of the ECG curve:

1. In one test subject there were noticed before medication in the ECG at rest precordial T-flattenings at the left side which rose again under stress and which could not be seen any more after medication.

2. In the other test subjects there were found before administration of substance one, and after administration three extra systoles per minute.

The ECG of the athletic test person did not show any alterations due to the substance.

After administration of substance the systolic blood pressure of the five untrained test subjects at rest was on the average 9 mm Hg, under 50 to 150 watt-stress on the average about 8–15 mm Hg, after recovery about 11 mm Hg on the average, below the control value. The maximum single decrease amounted to 25 mm Hg. Two of the five test subjects did not show any decreases under higher stress stages, compared to the control value. In the athletic test subject the systolic blood pressure decreased after medication at rest and after recovery by each 20 mm Hg and under the various stress stages by 10 to 30 mm Hg, compared to the control value.

Under the 50 watt-stress, and after having taken the compound the diastolic blood pressure fell in five of the untrained test subjects by 5 to 10 mm Hg, and in the athletic test subject by 10 mm Hg compared to the control value. At rest, under the remaining stress steps and after recovery all the six test persons did not show distinct changes due to the substance.

Under medication, four of the five untrained test subjects felt a slight weariness. One of the test persons managed the Ergometry-stress more easily after ingestion of the preparation, the other one more difficulty than before medication. The athletic test subject related under effect of the compound a slight sedation, a slight dryness of the mouth and a greater strain under stress than before medication.

In a further clinical test the blood pressure of two test persons was measured at a suitable time (Riva-Rocci), the ECG was registered (at rest, leads from extremities and chest-wall, under stress only chest-wall leads) and therefrom the heart rate was calculated:

After determination of the values while lying at rest, the test subjects were exposed to increased stress on the bicycle ergometer. The starting values were 25 and 50 watts respectively, and after each 3 minutes the stress was raised by 25 watts, up to 125 and 150 watts, respectively. 3 minutes afterwards, the "recovery-values" were determined. In the morning of the 1st test day a control test was made. Then, the test subject took 80 mgm of active substance per os. 3 days later, 40 mgm of active substance were taken in the morning, and two hours later a stress test was made.

By means of 2-[N-(2,6-dichlorophenyl)-N-allyl-amino]-imidazoline the heart rate of both test persons was decreased, independent of the dose, at rest as well as under stress. In one subject even the recovery values were lower after taking the substance. In the other test subject the systolic blood pressure was decreased at rest, under stress and during the recovery phase by means of the substance; the diastolic blood-pressure did not show any significant changes. After taking the substance (both doses) the systolic blood pressure decreased noticeably at rest. With increasing stress, the systolic blood pressure also increased and reached 100 watts approximately the values of the control test.

After 80 mg the recovery value was clearly lower than in the control test. The diastolic blood pressure was decreased at rest, under stress it did not show uniformity. In the ECG, after taking the substance no changes were observed, except a sinus bradycardia.

For both test subjects the substance was compatible without symptoms.

In view of the good compatibility of 2-[N-(2,6-dichlorophenyl)-N-allyl-amino]-2-imidazoline, the substance is suitable for use in prophylaxis and therapy of ischemic diseases and in patients having sinus tachycardia of various origins.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of slowing the heart rate of a warm-blooded animal in need thereof, which comprises perorally or parenterally administering to said animal an effective bradycardiac amount of 2-[N-(2,6-dichlorophenyl)-N-allyl-amino]-2-imidazoline or a non-toxic, pharmacologically acceptable acid addition salt thereof.

2. The method of claim 1, wherein said effective bradycardiac amount is 0.083 to 0.83 mgm/kg.

* * * * *